United States Patent [19]

Nehring, John R.

[11] 4,136,696
[45] Jan. 30, 1979

[54] SELF-CONTAINED, COMBINED IRRIGATOR AND EVACUATOR FOR WOUNDS

[75] Inventor: John R. Nehring, Woodcliff Lake, N.J.

[73] Assignee: International Paper Company, New York, N.Y.

[21] Appl. No.: 729,094

[22] Filed: Oct. 4, 1976

Related U.S. Application Data

[63] Continuation-in-part of Ser. No. 568,205, Apr. 5, 1975, Pat. No. 3,983,872, and Ser. No. 587,142, Jun. 16, 1975, Pat. No. 4,022,209, each is a continuation-in-part of Ser. No. 417,124, Nov. 19, 1973, Pat. No. 3,889,677.

[51] Int. Cl.² ............................................. A61M 1/00
[52] U.S. Cl. .................................................. 128/278
[58] Field of Search ............................... 128/276–278, 128/214 F, 231, 214 R, 207; 222/386.5; 417/383, 389, 394; 138/30; 141/7, 65, 67; 137/256

[56] References Cited

U.S. PATENT DOCUMENTS

| 1,245,845 | 11/1917 | White | 128/278 |
| 2,074,223 | 3/1937 | Horiuchi | 128/214 R |
| 3,291,151 | 12/1966 | Loken | 137/256 |
| 3,398,743 | 8/1968 | Shalit | 128/231 |
| 3,592,636 | 7/1971 | Scwarztman | 222/207 |
| 3,809,086 | 5/1974 | Schachet et al. | 128/278 |
| 3,983,872 | 10/1976 | Nehring | 128/278 |
| 3,993,069 | 11/1976 | Buckles | 128/214 F |

Primary Examiner—Robert W. Michell
Assistant Examiner—V. Millin
Attorney, Agent, or Firm—Finnegan, Henderson, Farabow & Garrett

[57] ABSTRACT

A self-contained, combined irrigator and evacuator for wounds comprising a container and a resilient inflatable bladder within the container, the container and inflatable bladder having a combined configuration which avoids unnatural deformation of the inflatable bladder by the container in at least one direction of expansion. The bladder is expanded against its bias by filling with an irrigation fluid, the bias causing pumping of the fluid from the bladder to the patient for wound irrigation while simultaneously effecting a negative pressure in the container for evacuation of fluid from the wound site and collection of the evacuated fluid in the container.

23 Claims, 23 Drawing Figures

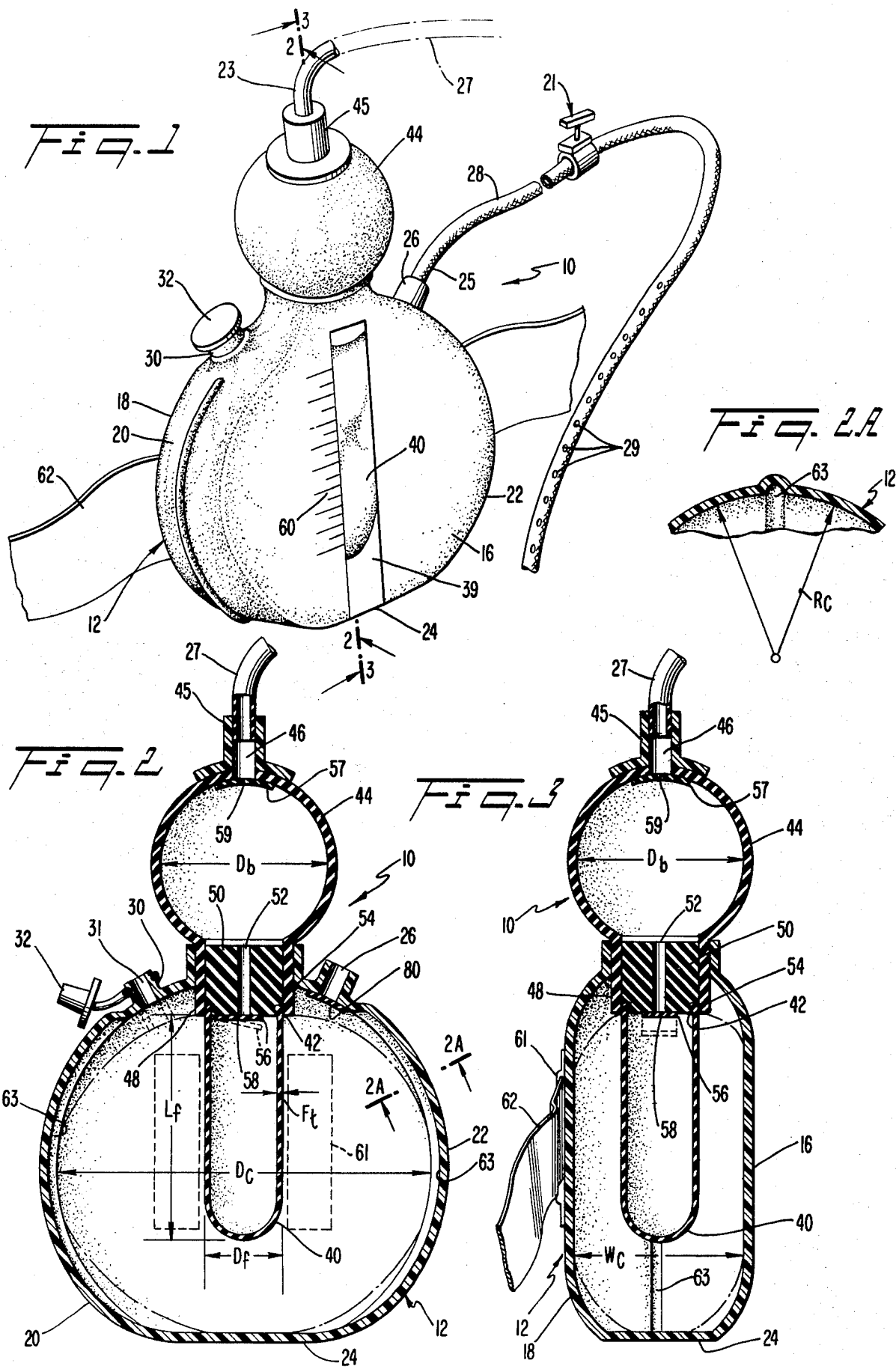

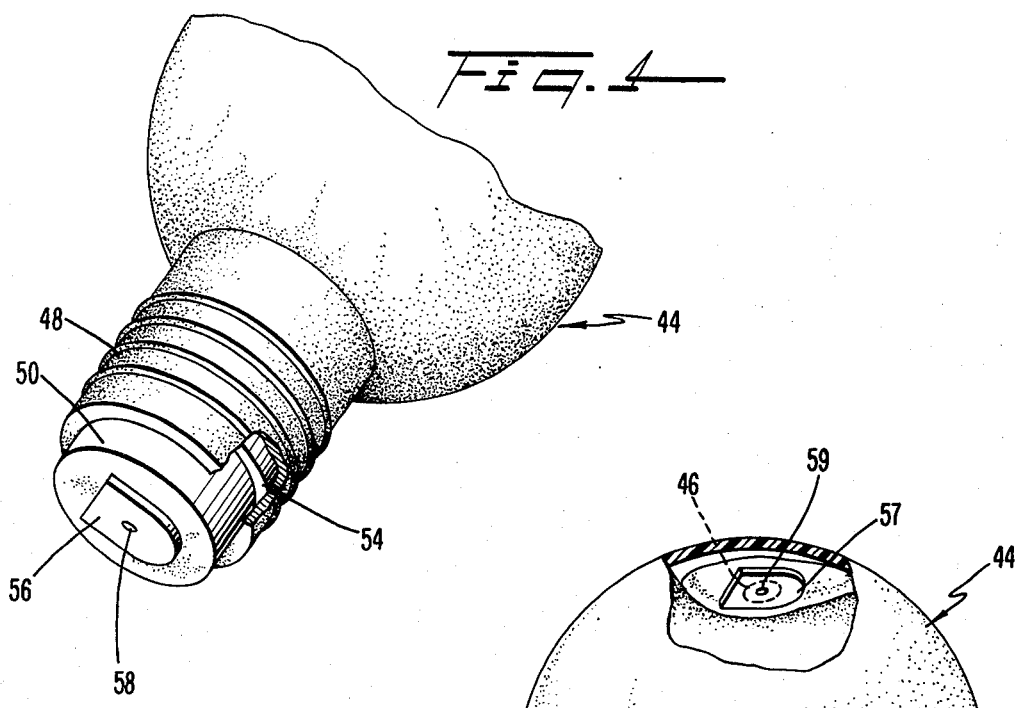
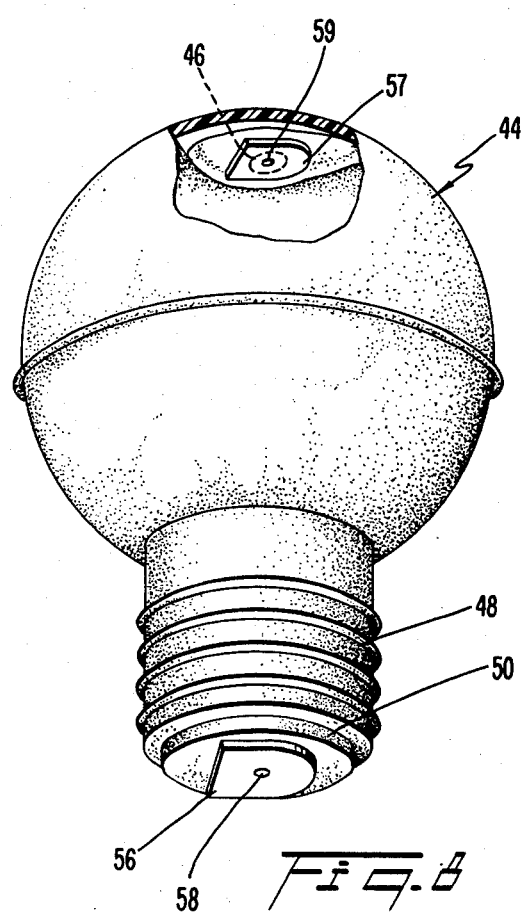
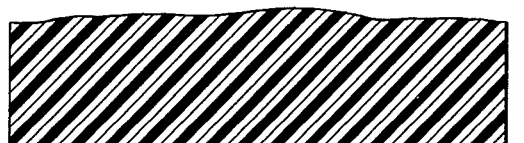

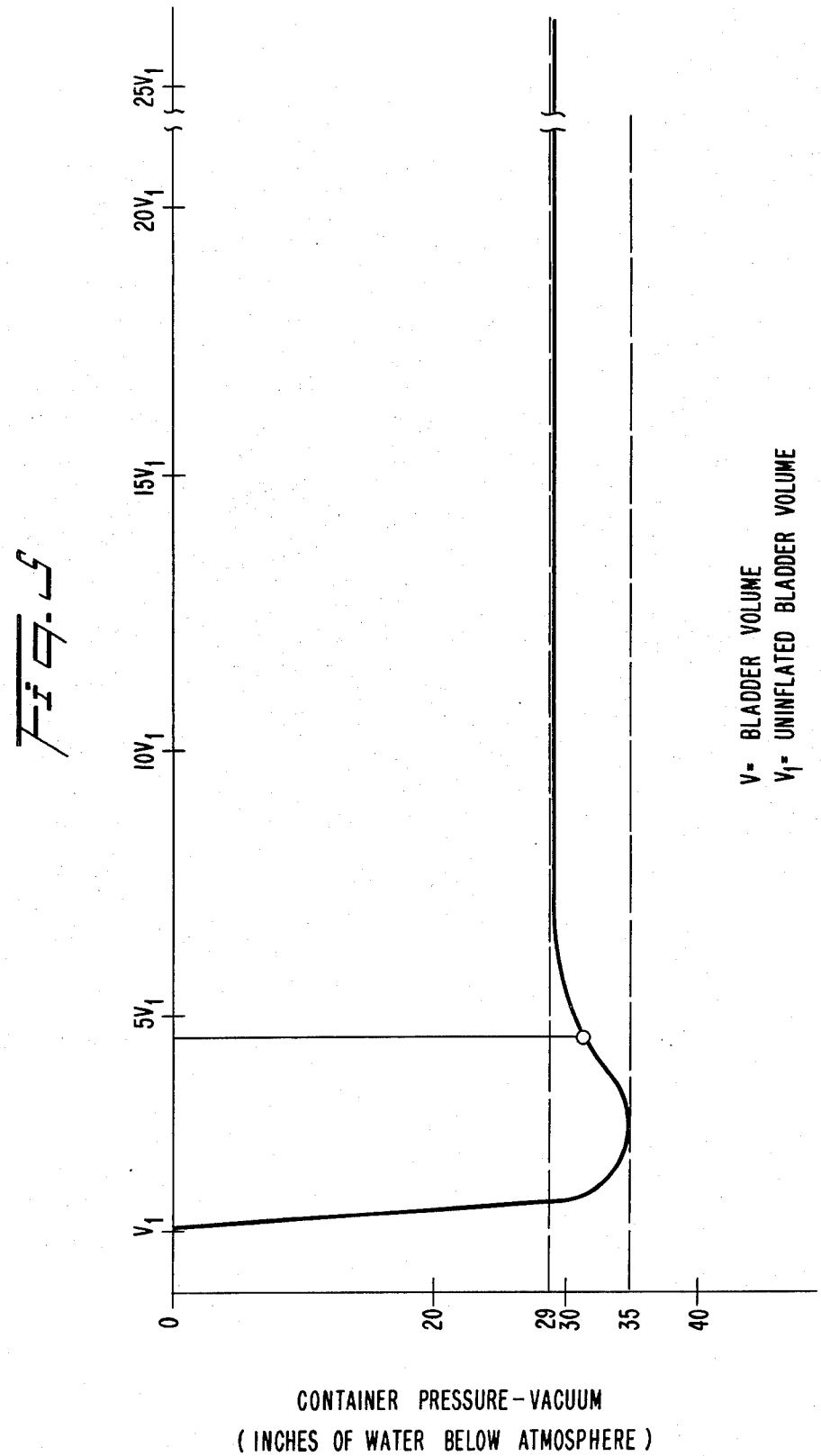

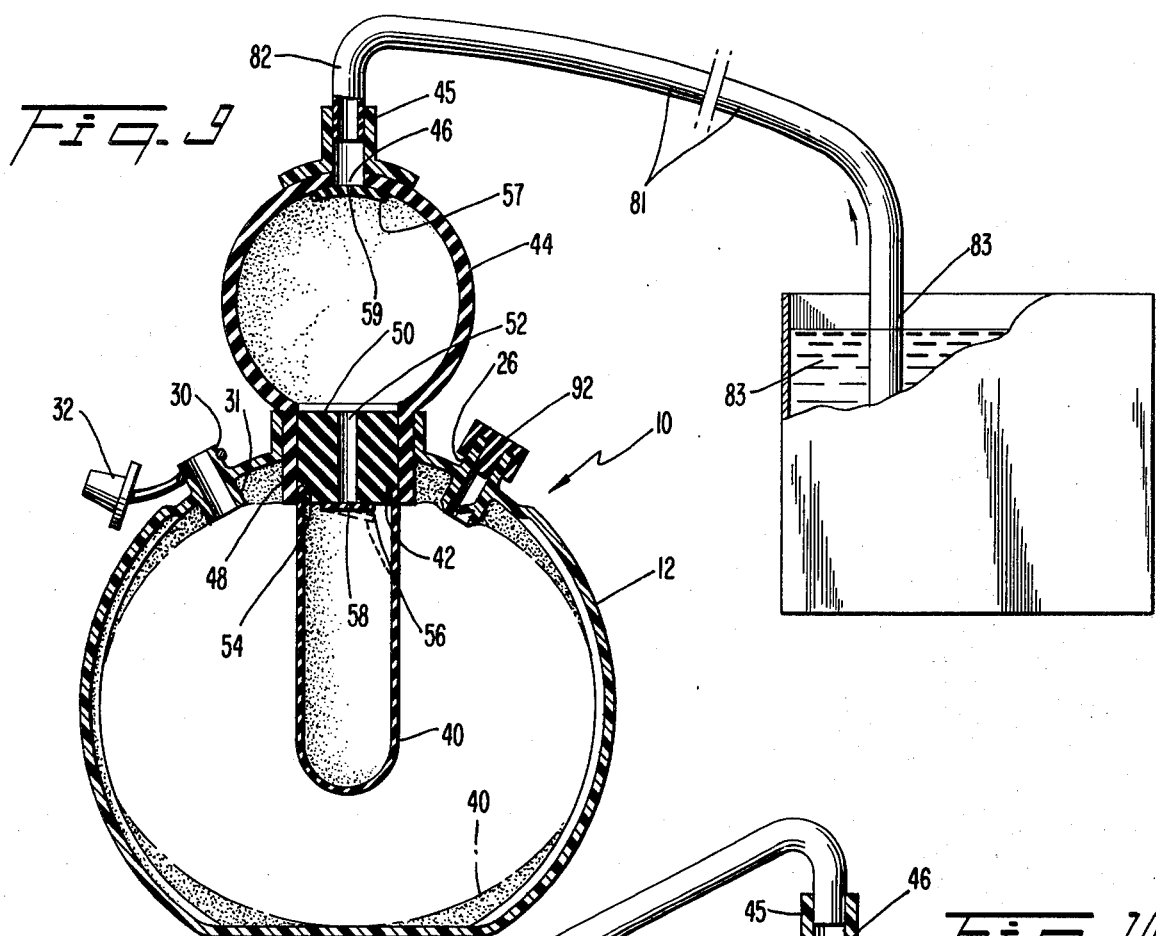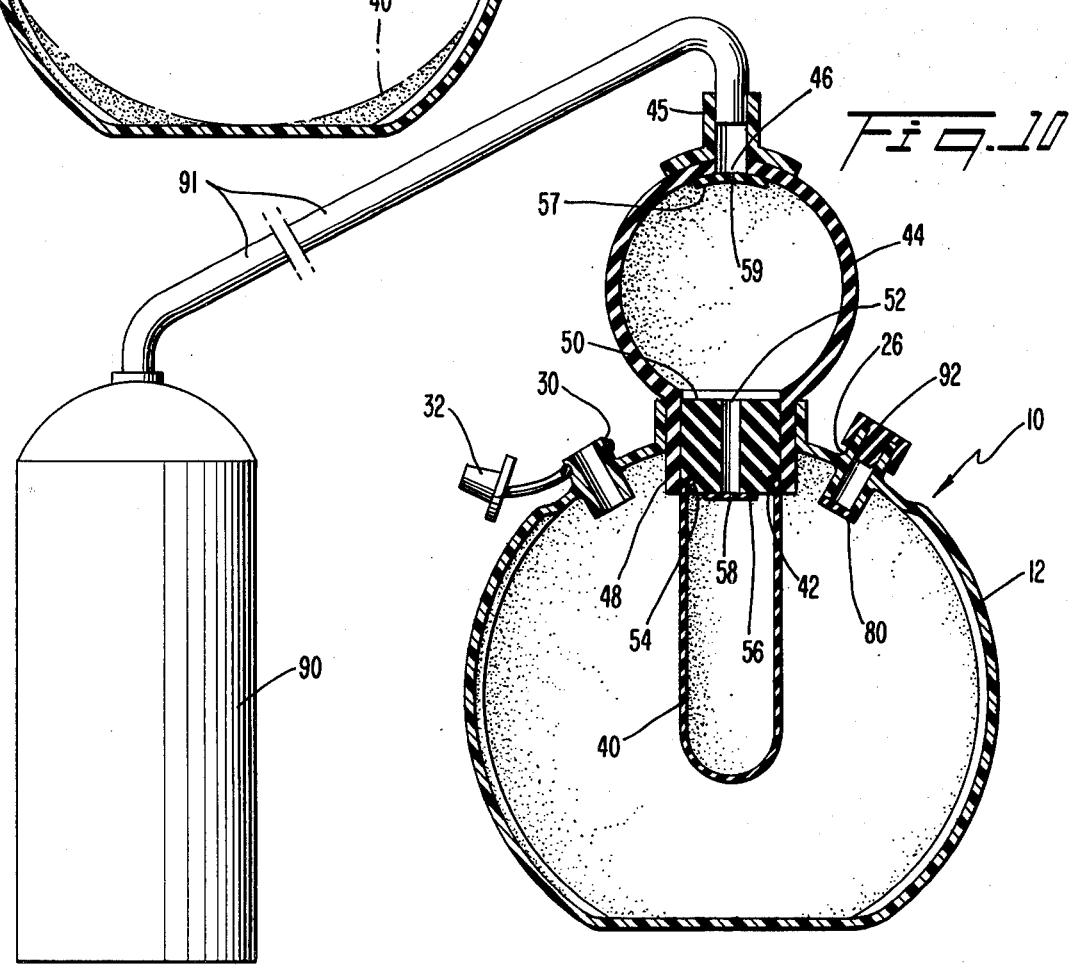

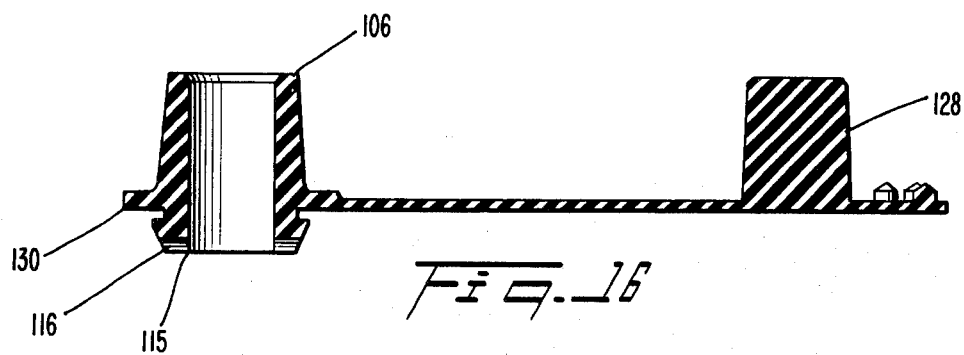
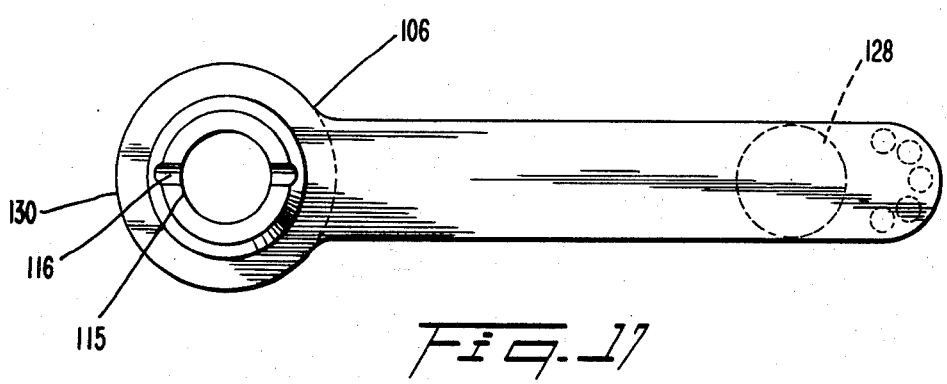
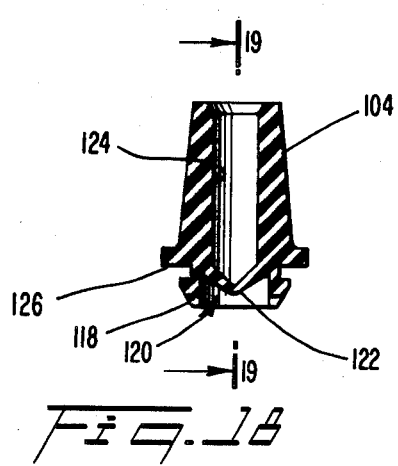
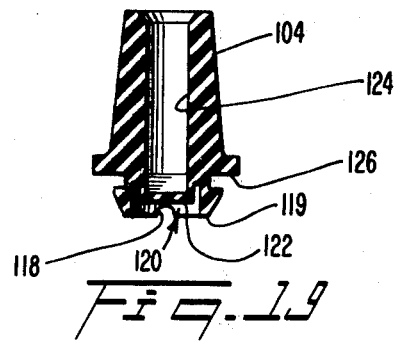
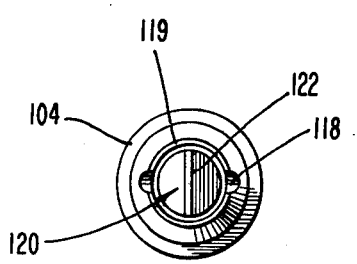

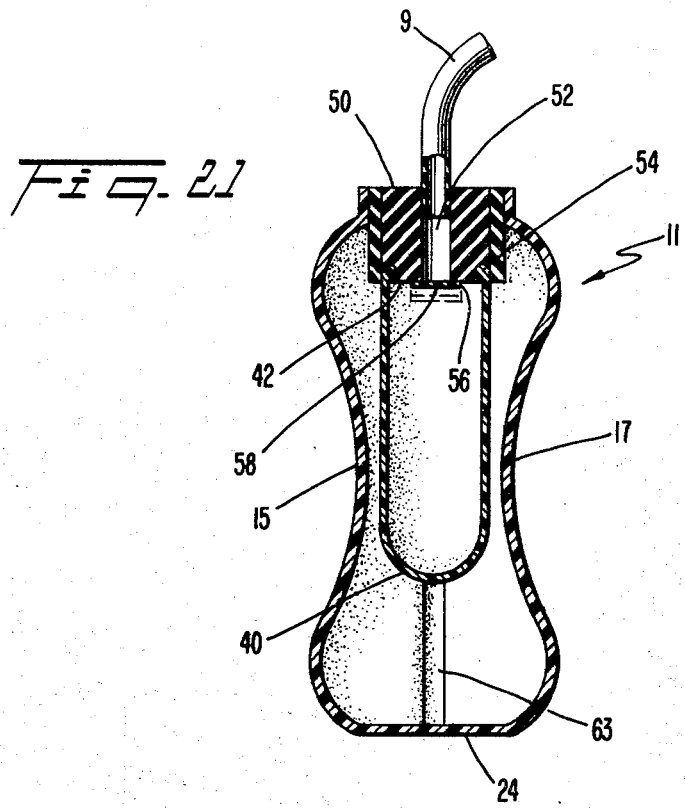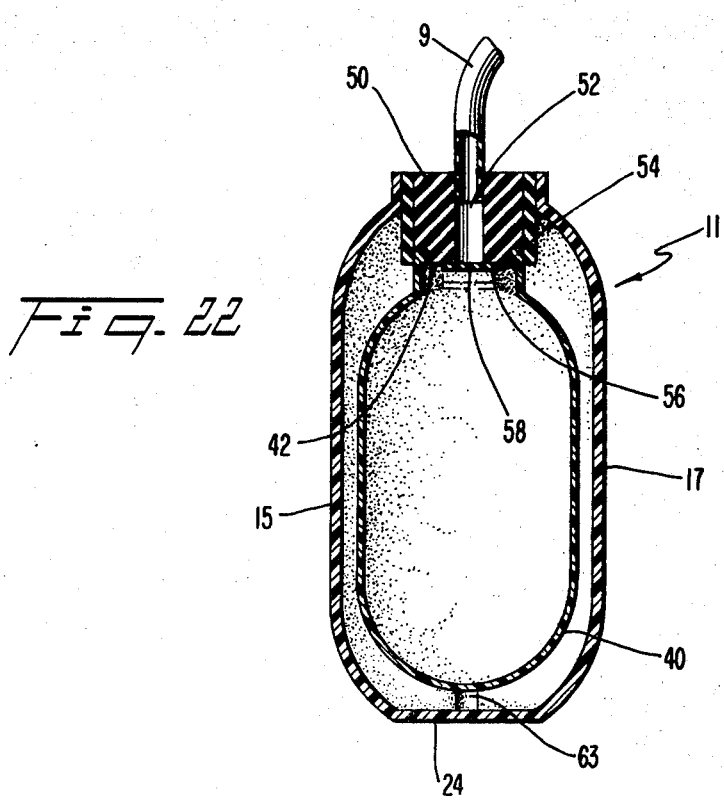

SELF-CONTAINED, COMBINED IRRIGATOR AND EVACUATOR FOR WOUNDS

This is a continuation-in-part of Application Ser. No. 568,205, filed Apr. 15, 1975 which issued as U.S. Pat. No. 3,983,872 on Oct. 5, 1976 and of co-pending application Ser. No. 587,142 filed on June 16, 1975 which issue as U.S. Pat. No. 4,022,209 on May 10, 1977, both of which are continuations-in-part of application Ser. No. 417,124, filed Nov. 19, 1973 which issued as U.S. Pat. No. 3,889,677 on June 17, 1975.

BACKGROUND OF THE INVENTION

1. Field of the Invention

This invention relates to medical apparatus for cleansing internal wounds; more particularly, it relates to a self-contained, disposable, portable, combined wound irrigator and evacuator.

2. Description of the Prior Art

The evacuation of fluids from a closed wound is a common medical practice. This is often done on completion of surgery. Fluid evacuation usually is accomplished through gravity drainage, pressure dressings or compression bandages or by negative pressure or suction, the latter being preferred. Conventional closed wound suction devices include power driven vacuum pumps, central suction systems, or evacuated bottles. While each of these evacuation systems effectively evacuates a wound, all except the evacuated bottles have many disadvantages because of their cost, noise and restriction on patient mobility resulting in the retardation of post-operative exercises, ambulation and rehabilitation. The evacuated bottle may provide mobility but has the disadvantages of cost and the necessity of having to have many available since when one bottle fills, it must be replaced. The filled bottle must be emptied, sterilized and re-evacuated.

In addition to evacuating fluids from a closed wound, it is frequently necessary to expose the wound site to a flow of an irrigating solution to bathe the infected area. This has been particularly true in the case of chronic osteomyelitis. In the past, wound bathing has generally been accomplished by means of gravitational flow, such as through an intraveneous device. Irrigation in this manner further restricts patient mobility.

The frequent necessity of bathing and evacuating a wound site has accentuated the need for a device which will eliminate the cumbersome, complicated, expensive and restrictive combination of irrigation equipment and evacuation equipment.

The disadvantages of the previous wound evacuation systems have, in part, been overcome by recent inventions such as those shown in U.S. Pat. Nos. 3,774,611 and 3,779,243. In both of these devices the evacuator comprises an evacuation chamber formed with resilient side walls which, after manual compression and release, tend to return to their original position. During return to their original position, they provide a reduced pressure on the interior of the container which, when connected to an internal wound by means of a catheter tube, effects evacuation of the wound. While these inventions overcome the serious disadvantages of power-driven vacuum pumps and central suction systems, they have their own disadvantages. Their major disadvantage is the possibility of accidental compression of the container at a time when it is undesirable.

Another disadvantage includes the necessity of inverting the container and compressing it to empty for re-use since this may disturb the patient. Furthermore, these devices are deficient in that they serve only one purpose, namely the removal of fluids from the wound. Thus, although these evacuation devices permit a certain amount of patient mobility, if wound irrigation is also necessary, the patient must be connected to a means for irrigating the wound, such as an intraveneous device. The necessity of combining the two systems, one for evacuation and one for irrigation, makes the entire system inconvenient, relatively expensive and cumbersome. While ostensibly a patient could be ambulatory by carrying an intraveneous bottle of irrigating fluid above his head and carrying or wearing an evacuator device, it is unlikely that such a situation would be considered a convenient solution.

Still another disadvantage of prior art evacuation devices is their wide variation of negative pressure over the specified filling range of the devices. When empty and fully compressed, these devices often provide a vacuum higher than necessary which might cause lesions if tissue is sucked into or against the drainage tube. On the other hand, as the container becomes filled with fluid, the vaccum is reduced often to a level where the vacuum is relatively ineffective and clots or other debris may clog the drainage tube. Wound evacuators presently commercially available have total pressure variations of about 130% or more.

This invention's co-pending Application Serial No. 618,482 filed Oct. 1, 1975, now U.S. Pat. No. 4,058,123, is an example of a device combining irrigation and evacuation that overcomes the disadvantages of the prior art. While this co-pending application serves the same advantageous function, the instant invention is significantly structurally different.

It is the disadvantages of the prior art with respect to mobility, expense, convenience, disposability, safety and utility that the present invention is intended to overcome.

BRIEF DESCRIPTION OF THE INVENTION

In accordance with the invention, as embodied and broadly described herein, the self-contained, combined irrigator and evacuator comprises a container having an irrigation port communicating with the interior of the container, a resilient, inflatable member within the container having a single opening, an inlet passageway and an outlet passageway communicating with the interior of the container, means for inflating and filling the inflatable member with irrigating solution, flow control means for enabling fluid to enter the inflatable member at a higher rate than fluid can leave the inflatable member, and means for sealingly attaching the inflatable member opening to the irrigation port.

By expanding against bias and filling the inflatable member with irrigating solution, the bias or resiliency of the inflatable member tends to expel the solution through the irrigation port. Releasing the irrigating solution from the inflatable member permits the inflatable member to return to its original position, automatically providing reduced pressure in the container exterior to the inflatable member. The reduced pressure is conducted to the wound through the inlet passageway of the container and aspirates fluid from the wound.

It is preferred that the container include first and second spaced apart opposed side walls, third and fourth spaced apart opposed side walls joined at the opposite ends of the first and second side walls, the third and fourth side walls being spaced apart a greater distance than the first and second side walls, and a bottom wall joined to all four side walls, the four side walls being joined together at their tops to form the irrigation port.

Preferably, the irrigator and evacuator includes a means for selectively opening and closing the outlet passageway and the inlet passageway and means on the inlet passageway for attaching a fluid conduit means thereto.

It is also preferred that the third and fourth side walls of the container have a configuration which substantially conforms to the natural, unimpeded shape of the adjacent portion of the inflatable member when inflated, deflation of the inflatable member effecting substantially constant negative pressure at said inlet passageway and providing positive irrigation pressure at the opening of the inflatable member. The first and second walls of the container are preferably flat in order to provide a low profile to the container.

In the preferred embodiment, the inflatable member is a substantially cylindrical, resilient bladder having a single opening.

While a specific location of the inlet and the outlet passageway in the container walls is not required, it is preferred that the inlet passageway be in one of the third and fourth side walls and the outlet passageway be in the other of the third and fourth side walls, the passageways being proximate to and on the opposite sides of the irrigation port.

A means for inflating the bladder is, preferably, a hand-operated, resilient bulbous member mounted exterior to the container having a neck portion defining an opening and a second opening opposite the neck opening, the resiliency of the bulbous member being greater than that of the bladder and the neck of the bulbous member being mounted in fluid flow communication with the opening in the bladder through the irrigation port.

While the flow control means can be any means that enables fluid flow into the bladder to be greater than fluid flow out of the bladder, it is preferred that the flow control means be two one-way check valves, each having a bleed valve therein, one check valve being mounted on and controlling flow through the second opening of the bulbous member and the other check valve being mounted and controlling flow through the neck opening.

Preferably, means for attaching fluid conduit to the second opening of the bulbous member is provided.

The preferred means for filling the bladder with irrigating solution comprises a filling fluid conduit attached at one end in fluid flow communication with the second opening in the bulbous member and at the other end in fluid flow communication with contained irrigating solution at atmospheric pressure such that repetitive squeezing and releasing of the bulbous member inflates the bladder against its resilient bias and fills it with the irrigating solution.

It may also be preferred to include in the irrigator and evacuator an irrigating fluid conduit and an evacuating fluid conduit, each of the conduits being open at a first end and having a plurality of openings at a second end, the second ends of both fluid conduits being utilized for placement in fluid flow communication with the fluid in the wound, the first end of the irrigating fluid conduit being attached to and in fluid flow communication with the second opening of the bulbous member for conducting irrigating solution expelled from the bladder to the wound and the first end of the evacuating fluid conduit being attached to and in fluid flow communication with the inlet passageway for conducting fluid from the wound to the container.

The preferred embodiment also includes an inwardly extending tubular protuberance around the outlet passageway, the protuberance extending into the container a distance calculated to bring it in contact with the bladder at the appropriate bladder inflation level.

The embodiments as described each meet the objective of providing an inexpensive, reliable, disposable or re-usable, portable, self-contained combined irrigator and evacuator.

Additional objectives and advantages of the invention will be set forth in part in the description which follows, and, in part, will be obvious from the description, or may be learned by practice of the invention. The objectives and advantages of the invention may be realized and obtained by means of instrumentalities and combinations particularly pointed out in the appended claims.

The accompanying drawings, which are incorporated in and constitute a part of the specification, illustrate an embodiment of the invention and, together with the description, serve to explain the principles of the invention.

BRIEF DESCRIPTION OF THE DRAWINGS

FIG. 1 is a perspective view of the combined irrigator and evacuator formed in accordance with this invention.

FIG. 2 is a sectional view taken along line 2—2 of FIG. 1.

FIG. 2A is a sectional view taken along line 2a—2a of FIG. 2.

FIG. 3 is a sectional view taken along line 3—3 of FIG. 1.

FIG. 4 is an enlarged, partially cut-away perspective view of the throat portion of the bulbous member formed in accordance with one form of this invention.

FIG. 5 is an empirical pressure versus volume curve of a cylindrical latex bladder within a rigid container formed in accordance with this invention.

FIG. 6 is an enlarged sectional view of a portion of the wall of the wound evacuator container having a roughened interior surface.

FIG. 7 is an enlarged sectional view of a portion of the wall of the wound evacuator container having a coating on the interior surface thereof.

FIG. 8 is an enlarged, partially cut-away perspective view of the bulbous member formed in accordance with the embodiment of the invention.

FIG. 9 is a sectional and schematic view of an embodiment of the irrigator and evacuator depicting a means for filling it with irrigation fluid.

FIG. 10 is a sectional and schematic view of an embodiment of the irrigator and evacuator depicting an alternate means of filling it with irrigation fluid.

FIG. 16 is a sectional view of the outlet port used in a wound evacuator of FIG. 14.

FIG. 17 is a bottom view of the outlet port of FIG. 16.

FIG. 18 is a sectional view of the inlet port used in the wound evacuator of FIG. 14.

FIG. 19 is a sectional view taken along line 19—19 of FIG. 18.

FIG. 20 is a bottom view of the inlet port of FIG. 18.

FIG. 21 is a sectional view of another embodiment of the invention.

FIG. 22 is another sectional view of the embodiment of FIG. 21.

DETAILED DESCRIPTION OF THE PREFERRED EMBODIMENT

Figure 11:
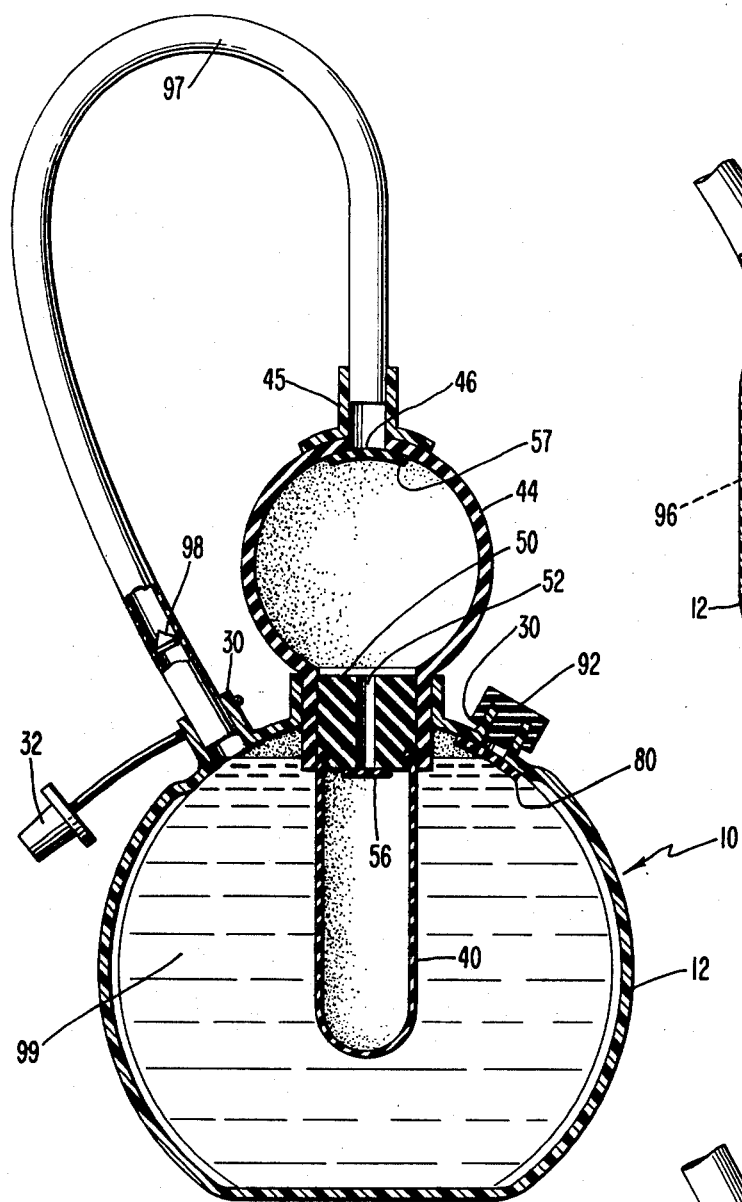
FIG. 11 is a sectional view of an embodiment of the irrigator and evacuator depicting means for storing the irrigating solution and for filling the irrigator and evacuator with the stored solution.

Throughout the specification and claims, terms of orientation, such as "front," "back," "up" and "down" are employed with respect to the orientations shown in the drawings in order to simplify description of the invention and are not intended to limit the location or direction of the elements with respect to which these terms are used.

The combined irrigator and evacuator of this invention permits bathing of a closed wound with an irrigating solution while simultaneously removing and collecting fluid from the closed wound. This is accomplished by utilizing a resilient, inflatable member contained within a container. The inflatable member is inflated and filled with the irrigating solution and, as the irrigating solution is expelled from the inflatable member to the wound by the force of the bias of the inflatable member, negative pressure is created in the container exterior to the inflatable member which, when communicated to the closed wound, aspirates fluid from the wound and collects it in the container.

In accordance with the invention, the combined irrigator and evacuator comprises a container having an irrigating port communicating with the interior of the container. As here embodied and depicted in FIGS. 1, 2 and 3, the self-contained irrigator and evacuator 10 is formed with the container 12 having opposed, spaced apart first and second side walls 16, 18 (hereinafter called "front and back walls"), opposed, spaced apart third and fourth side walls 20, 22 adjacent and joined to the opposite ends of the first and second side walls 16, 18, the third and fourth side walls 20, 22 being spaced apart a greater distance than the first and second side walls 16, 18, and a bottom wall 24. The four side walls 16, 18, 20 and 22 are joined together at the tops to form the irrigation port (unnumbered).

Preferably, the container 12 is substantially rigid, which means that it will not deform substantially when it is subjected to the normal forces to which devices of this sort are expected to be exposed.

The container 12 is provided with at least one passageway, such as passageway 26, extending through and communicating with the interior of the container 12. While a single inlet passageway 26 is sufficient for operation of self-contained irrigator and evacuator 10, it is preferred that a second passageway 30 be provided to serve as an outlet passageway to permit expulsion of air contained within the container 12 on inflation of the inflatable member and to permit removal of fluid which is received within the container 12 during utilization of the wound irrigator and evacuator 10. Preferably, means are provided for selectively opening and closing the outlet passageway 30 and the inlet passageway 26. As here embodied, a suitable closure or cap 32 is provided to permit the selective opening and closing of the outlet passageway 30 and a cap 92 (FIG. 10) is provided for selective opening and closing of the inlet passageway 26.

In accordance with the invention, a resilient, inflatable member having a single opening is provided within the container. As here embodied, the inflatable member is a resilient bladder 40 having an opening 42 at one end thereof. Preferably, and as depicted in FIGS. 1, 2 and 3, third and fourth side walls 20, 22 of the container 12 have a configuration which substantially conforms to the natural, unimpeded shape of the adjacent portion of the bladder 40 when inflated, deflation of the bladder 40 effecting substantially constant negative pressure at the inlet passageway 26 and providing positive irrigation pressure at the opening 42 of the bladder 40. It is also preferred that the front and back walls 16, 18 are substantially flat, thereby giving the container 12 a low profile.

In order to provide substantially constant negative pressure at the inlet passageway 26 throughout the entire operating range of the wound evacuator and irrigator 10, and to utilize substantially the entire volume of the container 12, the bladder 40 should have a combined actual or effective configuration so that the container 12 does not physically interfere with or distort the inflation of the bladder 40 in at least one direction of inflation. Terms "constant pressure" and "substantially constant pressure" as used throughout the specification and claims are intended for use in a relative sense and do not imply absolute constant or unchanging pressure. For example, a total pressure variation of up to about 20% to 30% throughout about 90% of the deflation range is acceptable.

A low profile container 12 (relatively narrow from front 16 to back 18) is preferred because it can be more comfortably and conveniently worn by a patient or attached to a support, such as a bed or a chair. These advantages can be obtained if the front and back walls 16, 18 are substantially flat and relatively closely spaced apart. Substantially flat front and back walls are walls which either are truly flat or which have a radius of curvature much greater than the radius of the bladder 40. Where a substantial vacuum is to be induced in the container 12, it may be preferred to form the front and back walls 16, 18 with a shallow outward curvature (large radius of curvature) to provide structural strength without adversely affecting the low profile of the container.

It is also desirable to be able to stand the container 12 vertically on a flat surface and, therefore, the bottom wall 24 of the container preferably should be flat.

It has been found that satisfactory constant pressure can be obtained with a cylindrical bladder when the bladder is inflated in a low profile container ("flat" front and back walls). The third and fourth side walls 20, 22 adjacent to the "flat" front and back walls 16, 18 actually or effectively conform to the shape of the inflated bladder 40.

In order to actually conform the third and fourth side walls 20, 22 to the bladder shape, the third and fourth side walls 20, 22, are formed with a transverse outward curvature (from front wall to back wall) as can be seen in FIG. 2A. Preferably, the radius of transverse curvature is $W_c/2$ where $W_c$ is the distance between the front and back wall 16, 18. It is also desirable to avoid corners at the top and bottom of the side walls and, therefore, rounded upper and lower ends are formed or, alternately, the side walls 20, 22 can be formed with a longitudinal curvature from top to bottom as can be seen in FIGS. 1 and 2.

While satisfactory results can be obtained over a relatively wide range of front-to-back wall spacings, more consistently reliable results and more useful filling volume for a given container size, while maintaining relatively constant pressure, can be obtained if the front and back walls 16, 18 are spaced apart a distance greater than twice the diameter of the uninflated bladder ($W_c > 2D_f$).

Instead of actually conforming the third and fourth side walls 20, 22 to the inflated bladder shape, the third and fourth side walls 20, 22 can be made to "effectively" conform to the bladder 40 by controlling the pressure within the container. More specifically, with the inlet passageway 26 closed as the bladder 40 is inflated, the air inside the container 12 is expelled through the outlet passageway 30 until after the bladder contacts the third and fourth side walls 20, 22 and if it continues to inflate, it reaches a position within the container 12 wherein the bladder 40 is about to be forced into a shape which is different from that it would be if the side walls 20, 22 were non-existent. At that time, passageway 30 is occluded by the bladder 40 to prevent further expulsion of air from the container 12. Any further pressurization of the bladder 40 results in a concomitent increase in pressure inside the container 12 since the air cannot escape. Upon release of the fluid input pressure to the bladder 40, the pressure in the bladder 40 and in the container 12 drops by virtue of fluid in the bladder 40 escaping through the bladder opening 42. This concept of pressure equalization in the container 12 and bladder 40 when the bladder 40 is about to be deformed into a shape which adversely effects the constant pressure curve is referred to throughout the specification and claims as "effective" confirmation of the container shape with the bladder shape. As used in the claims, the term "substantially conforms" includes both "actual" and "effective" conformation as defined herein.

Preferably and as here embodied, the outlet passageway 30 is occluded by the bladder 40 when it reaches a predetermined shape. This is effected by forming the outlet passageway 30 with an inwardly extending tubular protuberance 31 which projects into the container a distance calculated to bring it in contact with the bladder 40 at an appropriate bladder inflation level. The outlet passageway 30 and the protuberance 31 can be formed as an integral part of the container 12 or can be formed as a separate member mounted in an opening formed in the container 12. When outlet passageway occluding concept is employed, the shape of the container 12 is not critical.

With respect to a container which actually conforms to the bladder shape and which has a satisfactory low profile, substantially constant negative pressure during deflation of a bladder has been obtained with a container and latex cylindrical bladder having the shapes generally shown in FIGS. 2, 2A and 3 and having the following dimension ratios.

$D_f$ = diameter of bladder;
$L_f$ = length of bladder = 3.0–4.0 $D_f$
$W_c$ = width of container = 2.5 $D_f$
$R_c$ = radius of transverse curvature of side walls = $W_c/2$
$D_c$ = length of container = 1.8$L_f$
$P_c$ = container interior perimeter 22$D_f$ The bladder thickness ($F_t$) together with the characteristics of the bladder material (actually, the modulus of elasticity) determines the vacuum level produced within the container. For a latex bladder, a bladder thickness of 0.01$D_f$ has been found to produce a constant negative pressure in the above described container of approximately 30 inches of water (see FIG. 5). The container perimeter/bladder diameter ratio is calculated to provide not greater than a seven-fold increase in bladder perimeter which has been found to be within a safe stress range for a latex bladder. For a convenient and comfortable evacuator profile, the bulb diameter ($D_b$) should be approximately equal to the width of the container ($D_b = W_c$).

These ratios provide a self-contained wound irrigator and evacuator having satisfactory performance by providing relatively constant pressure in a desired pressure range (−29 to −35 inches of water) and a safe stress for a bladder made of natural latex. The bladder 40 can also be formed from any synthetic elastomer, such as polyurethane. FIG. 5 is a pressure vs. volume curve of a latex bladder having a ¾" uninflated diameter, a 2½" free length and a 0.012" wall thickness which was inflated in a rigid container having dimensions substantially in accordance with the above dimension ratios. As can be seen, the vacuum within the container remains between 31.3 inches of water at a bladder volume of about 4.5 times the uninflated bladder volume (4.5$V_1$) at which time the bladder 40 first touched the relatively close container walls (e.g. 16, 18) and 29 inches of water. The pressure remains at this level throughout the operating range of the irrigator and evacuator and satisfactory results have been obtained at bladder inflations of over 30$V_1$. The total pressure variation over this range was only about 8% of the minimum pressure within the range (29 inches of water). In connection with wound irrigators and evacuators, the pressure curve of FIG. 5 is considered to have a substantially constant pressure.

While a specific location of the inlet passageway 26 and the outlet passageway 30 is not required, it is preferred that the inlet passageway 26 be in one of the third and fourth side walls 20, 22 and the outlet passageway 30 be in the other of the third and fourth side walls 20, 22, the passageways 26 and 30 being proximate to and on the opposite sides of the irrigation port (unnumbered).

In accordance with the invention, means for inflating and filling the resilient bladder 40 is provided. As here embodied, the means for inflating and filling the bladder 40 is preferably a manually operated pump, such as a hand-operated, resilient bulbous member 44 having a resiliency slightly greater than the resiliency of the bladder 40. The bulbous member 44, being located exterior to the container 12, has a neck portion 48 defining an opening (unnumbered) and a second opening 46 opposite the neck opening. The neck portion 48 of the bulbous member 44 is mounted in fluid flow communication with the opening 42 of the bladder 40 through the irrigation port (unnumbered).

In accordance with the invention, means for sealingly attaching the bladder opening 42 to the irrigation port (unnumbered) is provided. As here embodied and depicted in FIGS. 2 and 3, the opening 42 of the bladder 40 is mounted in the neck portion 48 of the bulbous member 44 so that fluid expelled from the bulbous member 44 through the neck 48 is forced to enter the bladder 40. While the bladder 40 can be mounted directly to the walls of the neck portion 48 of the bulbous member 44, the embodiment illustrated in FIGS. 2-4 employs a plug 50 which is force-fitted within the neck portion 48, the plug 50 having a fluid passageway 52 axially therethrough. The plug is provided with an annular recess 54 to receive the opening 42 of the bladder 40, the open end of the bladder 40 being trapped between the exterior of the plug 50 and the interior of the neck portion 48 of the bulbous member 44 to fixedly hold and seal the bladder 40 in place.

While the second opening 46 of the bulbous member 44 is shown at the top of the bulbous member 44, it could be located at other convenient positions on the bulbous member 44.

Further in accordance with the invention, flow control means are provided which enable fluid to enter the bladder 40 at a higher rate than fluid can leave the bladder 40. Thus, when fluid pressure tending to enter the bladder 40 is greater than the fluid pressure within the bladder 40, the valve means permits free-flow of fluid into the bladder 40. However, when fluid pressure in the bladder 40 exceeds fluid pressure exterior the bladder opening 42, the flow control means restricts the flow rate from the bladder to a predetermined minimal quantity.

As here embodied, the flow control means comprises two one-way check valves each having a bleed valve therein. One check valve, such as a flapper valve 56 having a small diameter bleed vent 58 therethrough, is mounted on the bladder side of the plug 50. The other check valve, such as the flapper valve 57 having a small diameter bleed vent 59 therethrough, is mounted on the inside surface of the bulbous member 44 over the second opening 46. When the bulbous member 44 is squeezed, the flapper valve 56 permits the fluid in the bulbous member 44 to be freely expelled into the bladder 40 since the pressure differential across the flapper valve 56 during such an operation forces the flapper valve away from the plug 50 thereby permitting the fluid in the bulbous member 44 to flow easily into the bladder 40. When the bulbous member 44 is released, its resilient bias tends to return it to its original shape creating a partial vacuum within the bulbous member 44 and the flapper valve 57 permits fluid to flow through the second opening 46 into the bulbous member 44 since the pressure differential across the flapper valve 57 during expansion of the bulbous member forces the flapper valve 57 away from the inside surface of the bulbous member 44 permitting the fluid to flow easily into it.

When the bladder 40 is partially inflated and filled with fluid and the bulbous member 44 is returning from its squeezed or collapsed position to its normal or expanded position, the pressure within the bladder 40 is higher than the pressure within the bulbous 44 and the flapper valve 56 is forced against the plug 50 thereby obturating the fluid passageway 52 except for the vent 58 and preventing most of the fluid from leaving the bladder 40. Likewise, when the bulbous member 44 is squeezed, the fluid pressure inside the bulbous member 44 is greater than the fluid pressure outside the second opening 46 and the flapper valve 57 is forced against the inside surface of the bulbous member 44 thereby obturating the second opening 46 except for the vent 59 and preventing most of the fluid from leaving the bulbous member 44.

After the bladder 40 is fully inflated, the small bleed valves 58, 59 permit fluid to be expelled from the bladder 40 through the passageway 52, through the bulbous member 44 and through the passageway 46 at a predetermined rate.

Preferably, means is provided on the second opening 46 for attaching a fluid conduit in fluid-flow communication with the second opening 46. As here embodied, a tubular extension 45 is mounted on the bulbous member 44 over the opening 46 providing fluid flow communication with the interior of the bulbous member 44.

As here embodied and as depicted in FIG. 9, the means for filling the bladder also comprises a filling fluid conduit 81 being at one end 82 attached to and in fluid flow communication with the second opening 46 of the bulbous member 44 and at the other end 83 being in fluid flow communication with contained irrigating solution 84 at atmospheric pressure. With the outlet passageway 30 open, repetitive squeezing and releasing of the bulbous member 44 inflates the bladder 40 against its resilient bias and fills it with the irrigating solution 84.

It may be preferred to fill the bladder 40 with irrigating solution from a pressurized source 90 (FIG. 10). This means of filling the bladder 40 requires a filling fluid conduit 91 placing the second opening 46 in fluid flow communication with the source of irrigation fluid at pressure 90. Filling is accomplished by obturating the inlet passageway 26 either solely by means of the check valve 80 or, in addition, adding a cap 92. The outlet passageway 30 is open to permit expulsion of the air from the container 12. When the bladder 40 is full, the outlet passageway 30 is closed by the cap 32 and the filling fluid conduit 91 is replaced by the irrigating fluid conduit which provides fluid flow communication with the wound.

Another preferable means for filling the bladder 40 is as depicted in FIG. 9, to join the second opening 46 in fluid flow communication with irrigation fluid at atmospheric pressure 84 and to apply an external vacuum (not shown) to the outlet port 30. By obturating the inlet passageway 26, as with cap 92, and applying the vacuum to the outlet passageway 30, the reduction in pressure in the container 12 causes expansion of the bladder 40 and, therefore, the reduction in pressure within the bladder 40 aspirates irrigation fluid from the contained irrigation fluid 84 at atmospheric pressure.

As here embodied, the inlet passageway 26 includes a one-way check valve which precludes expulsion of air from the container 12 during expansion and filling of the bladder 40.

The check valve also serves to protect against accidental ejection of fluid through the inlet passageway 26. The one-way check valve, such as a flapper valve 80, can be mounted on the inlet passageway 26 for closing the inlet passageway 26 upon pressurization of the container 12. Such accidental ejection of accumulated fluids in the container may occur if the bulbous member 44 is accidentally squeezed. Of course, the check valve 80 does not interfere with the flow of fluid into the container 12. Furthermore, the inlet passageway 26 can be formed such that the bladder 40 occludes the port 26 when the bladder is inflated to its intended volume to further insure against leakage through passageway 26 to the patient.

The preferred embodiment also includes an irrigating fluid conduit 27 and an evacuating fluid conduit 28, each of the conduits being open at their first ends 23, 25 and having a plurality of openings 29 at the second end thereof for being placed in fluid flow communication with fluid in the wound. The first end opening 23 of the irrigating fluid conduit 27 is attached to and in fluid flow communication with the second opening 46 of the bulbous member 44 for conducting the irrigating solution expelled from the bladder 40 to the wound. The first end opening 25 of the evacuating fluid conduit 28 is attached to and in fluid flow communication with the inlet passageway 26 for conducting fluid from the wound to the container 12, thus, irrigating solution contained in the expanded or inflated bladder 40 is forced from the bladder by the bias of the bladder through the bleed valve 58, through the passageway 52, through the bulbous member 44, through the bleed valve 59, through the second opening 46, through the tubular extension 45 and through the irrigating fluid conduit 27 to the wound. As the fluid is expelled from the bladder 40, reduction in the bladder volume, with the outlet passageway obturated by the plug or cap 32, creates a negative pressure in the container 12 which is conducted through the inlet passageway 26 and through the evacuating fluid conduit 28 to the wound to aspirate fluid from the wound and collect the fluid in the container 12.

The irrigating fluid conduit 27 and the evacuating fluid conduit 28 are conventional flexible tubing that are non-toxic, non-pyrogenic, inert, non-porous and non-degradable when used in its intended environment.

The container 12 can be formed of any suitable material such as a moldable plastic, for example, polyvinyl chloride. The shape of the container lends itself to being blow molded; however, it could be formed other ways, such as by injection molding. At least a portion 39 of one of the flat side walls 16, 18 preferably is transparent and a calibrated graduated scale 60 is placed along the side thereof in order to enable volumetric measurement of the amount of fluid contained within the container 12. The container 12 also can be provided with mounting tabs 61 to which a belt 62 or other support means is attached to facilitate hanging the irrigator and evacuator 10 on a bed or chair or to enable the evacuator to be worn by an ambulatory patient.

Further in accordance with the invention, it is desirable to provide means for preventing accidental sealing off of a portion of the container 12 from the outlet passageway 30, especially during evacuation of fluids from the container 12 which were removed from the patient. One means for avoiding this blockage is to provide a recess 63, as illustrated in FIGS. 2 and 2A, in the interior surface of the container walls, particularly in the area leading to and adjacent to the outlet passageway 30. Such a recess 63 assures the existence of a fluid flow passageway from the interior of the container 12 to the outlet passageway 30. Also, the interior surface of the container walls can be roughened, such as by injection molding the container, to accomplish the same results (FIG. 6).

A means for minimizing bladder 40 stress is to provide a surface coating 64 on the interior surface of the container 12, (FIG. 7) or on the exterior surface of the bladder 40, which will lessen adherence of the bladder to the interior of the container. For example, it has been found that chlorinating the surface of a latex bladder or coating the interior surface of a container with a conventional commercially available medical silicone fluid successfully lessens adherence of the bladder to the container walls. Reduction of the adherence of the bladder 40 to the container walls also is of substantial assistance in maintaining the negative pressure substantially constant.

It is contemplated that the bulb member 44 can be of a size having the same capacity as the fully inflated bladder 40. In other words, a single compression of the bulbous member 44 filled with fluid would be sufficient to complete inflation and filling of the bladder 40.

Preferably, the combined irrigator and evacuator also includes a means for storing the irrigation solution which comprises a transfer fluid conduit means 97 (FIG. 11) providing fluid flow communication between the outlet passageway 30 and the second opening 46 of the bulbous member 44 and a one-way flow control means 98 located in the fluid flow path of the transfer fluid conduit means 97 permitting fluid flow through said transfer fluid conduit means 97 from the outlet passageway 30 to the second opening 46 of the bulbous member 44. The irrigating solution 99 can, therefore, be stored within the container 12 external to the bladder 40 and when the irrigator and evacuator 10 is prepared for use, the irrigating solution 99 is pumped from the container 12 through the outlet passageway 30, the transfer fluid conduit means 97, and the second opening 46 into the bladder 40 by repetitive squeezing and releasing of the bulbous member 44. The embodiment of the irrigator and evacuator depicted in FIG. 11 provides a means for factory preparation of a complete self-contained irrigator and evacuator.

Figure 12:
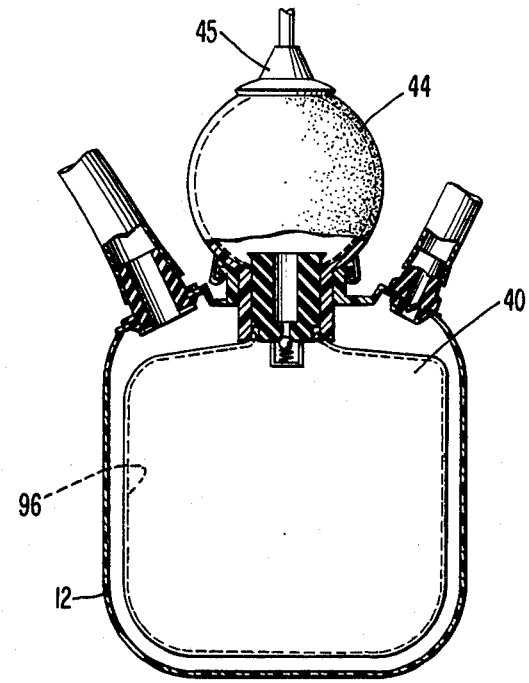
FIG. 12 is a sectional view of an embodiment of the irrigator and evacuator depicting a means for pre-filling and storing the irrigating solution within the irrigator and evacuator.

It may also be preferred to pre-inflate and fill the bladder 40 with irrigating solution at the factory level. This also provides self-contained irrigation and evacuation units without the necessity of external irrigation fluid sources. The potential disadvantage of the method of storing the fluid in the expanded bladder is the liquid loss through the bladder walls by vapor transmission. As here embodied, this disadvantage is overcome, as depicted in FIG. 12, by coating the inside wall of the bladder 40 and the inside wall of the bulbous member 44 with a material that prevents or reduces the vapor transmission loss. This material is preferably one having low vapor permeability.

The coating 96 could be applied prior to bladder inflation if the coating 96 is such that it will stretch sufficiently during bladder inflation to ensure adequate surface coverage after inflation. Alternatively, the coating 96 could be applied after inflation and the bladder 40 kept inflated thereafter through factory pre-fill operation. If, however, the coating 96 is a non-friable material which does not signficantly affect the bladder pressure curve and holds tenaciously to the inside surface of the bladder 40 during collapse, there is no need to maintain the bladder inflated during post-surface treatment operation.

Figure 13:
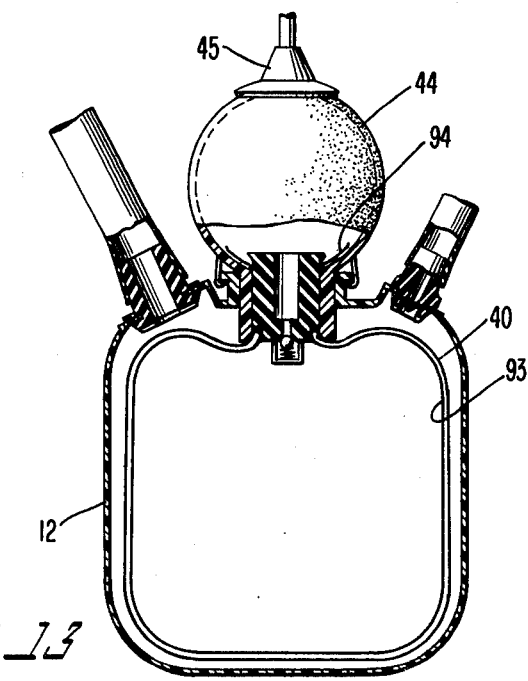
FIG. 13 is a sectional view of an embodiment of the irrigator and evacuator depicting another means of pre-filling and storing irrigating solution within the irrigator and evacuator.

Another means of precluding vapor transmission loss from irrigation solution stored within the bladder is depicted in FIG. 13. In this embodiment, the irrigating solution is contained within a relatively thin and flexible film material 93 having low vapor permeability of such a shape that when freely expanded by filling the bladder 40 with the irrigating solution at atmospheric pressure, it approximately corresponds to that of the fully expanded enclosing bladder 40 within the container 12. As can be seen in FIG. 13, the film or liner 93 is substantially a bag within the bladder 40 having a single opening 94, the opening 94 being hermetically affixed to the bulbous member neck 48, either mechanically or adhesively. In order to ensure maximum volume of irrigating fluid contained in the pre-filled bladder 40, it is necessary to ensure a minimum of air trapped between the liner 93 and the inside bladder wall.

It should be understood that the above described measures for reducing or eliminating irrigation solution vapor loss and direct contact of the bladder 40 and irrigation solution may be applied with equal effectiveness to the embodiment shown in FIG. 11 by coating or lining the outside wall of the bladder 40.

Figure 15:
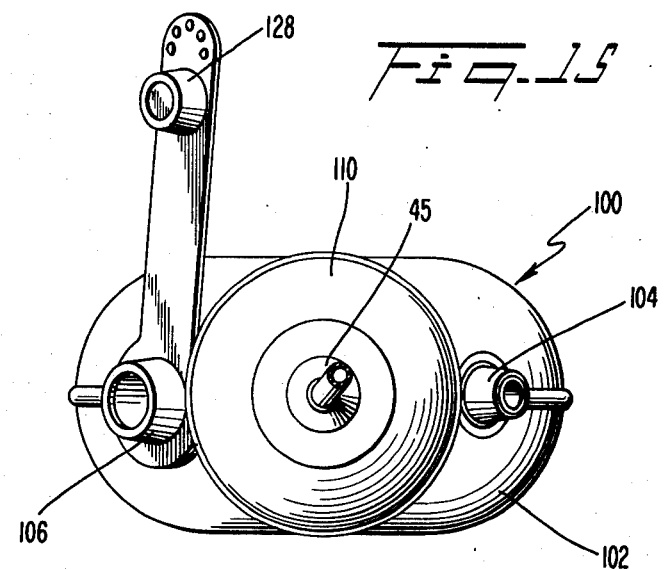
FIG. 15 is a top view of the wound irrigator and evacuator of FIG. 14.
Figure 14:
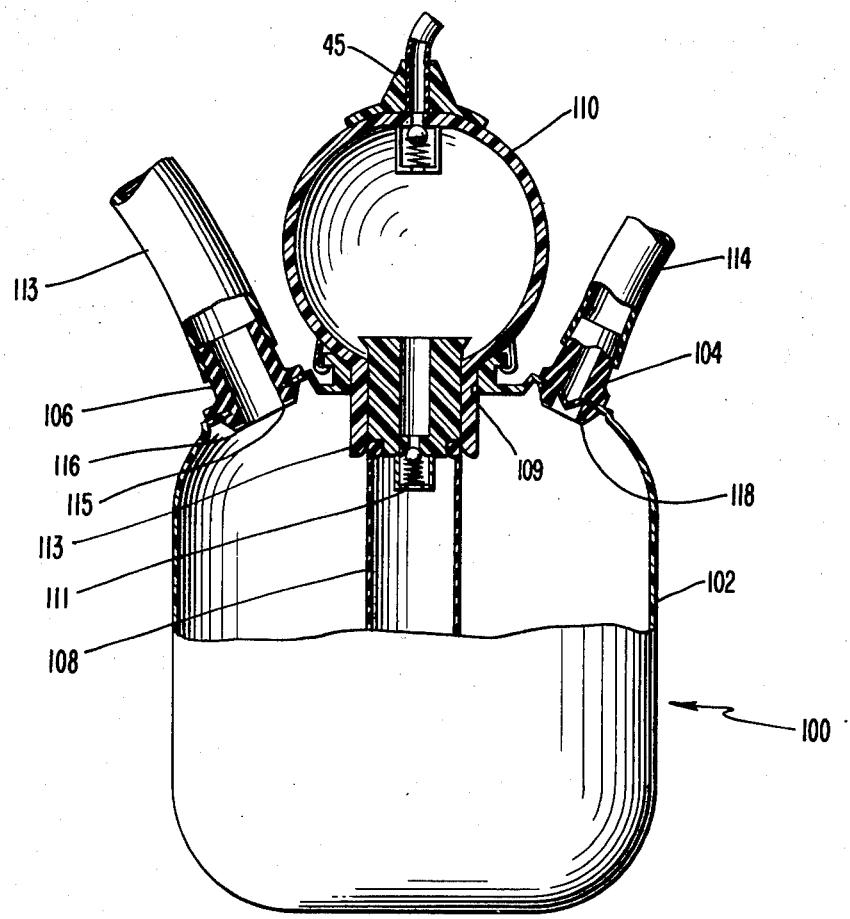
FIG. 14 is a partial sectional view of a combined wound irrigator and evacuator formed in accordance with another embodiment of this invention.

FIGS. 14 and 15 depict another embodiment of the wound irrigator and evacuator as claimed herein. The self-contained wound irrigator and evacuator 100 is formed with a container 102 having an inlet passageway 104 and outlet passageway 106 extending through and communicating with the interior of the container 102. The inlet and outlet passageways 104, 106 may be formed as an integral part of the container 102 (as illustrated in FIG. 2) or may be formed as separate members mounted in openings formed in the container 102 as illustrated in FIG. 14.

An inflatable member, for example, a resilient bladder 108 within the container 102 is attached to means for inflating the bladder 108, such as the hand-operated bulbous resilient member 110 having a neck portion 113 defining an opening and a second opening 115 opposite the neck opening. The neck 113 is mounted in an opening 109 through the container 102. The bulbous member is provided with flow control means between the bulbous member 110 and the bladder 108 and on the second opening 115, each permitting free flow fluid into the bladder 108 at a higher rate than fluid may flow from the bladder 108.

The flow control means may be any suitable imperfect check valve. For example, check valves 111 and 112 having either a roughened surface or a roughened valve seat would permit a limited flow rate from the bladder 108 to the bulbous member 110 and from the bulbous member 110 through the second opening 115. Another means is to provide a small bleed passageway through or on the side of the check valve or seat.

As explained with respect to the embodiments illustrated in FIGS. 1-8, the bladder 108 is expanded by squeezing the bulbous member 110 and forcing fluid into the bladder 108, the air between the bladder 108 and the container 102 interior walls being forced out through the outlet passageway 106. When the bladder 108 is fully expanded, the outlet passageway 106 is closed by the plug 128 and fluid is permitted to leave the bladder through its check valve 111 at a controlled rate causing a reduced pressure to exist at the inlet passageway 104 providing the necessary suction to remove fluid from the patient. When the container 102 is full, it must be emptied and the bladder 108 re-inflated and refilled, and the process repeated.

As illustrated in FIGS. 16-20, the inlet passageway 104 may be formed as a separate member such as by molding. The inlet passageway 104 also includes a check valve 120 integrally formed as a part thereof. The check valve 120 is formed by molding a V-shaped wall or disc 122 across the fluid channel 124 through the inlet passageway 104 and subsequently slitting the V-shaped wall 122 at its apex, thereby forming two flaps or lids. In this manner, when a pressure differential across the check valve 120 is such that the lower pressure is in the container 102 as contrasted with the inlet fluid channel 124, such as when fluid is being removed from the patient, the slit opens and fluid is permitted to pass therethrough. However, if pressure within the container 102 exceeds the pressure within the inlet fluid channel 124, pressure will tend to force the lips of the V-shaped wall 122 together, thereby closing the slit and preventing fluid flow from the container 102 into the inlet through channel 124 and ultimately to the patient. The check valve 120 is recessed with respect to the mouth 119 of the inlet passageway 104 to ensure that the bladder 108 does not interfere with the proper operation of the check valve 120. An annular groove 126 also is formed near the mouth 119 of the inlet passageway 104 to permit the inlet passageway 104 to be snap-fitted into an aperture through the walls of the container 102.

The outlet passageway 106 can also be molded as a separate member (FIGS. 16 and 17) and a closure plug 128 can be formed as an integral part thereof. An annular groove 130 is formed adjacent the mouth 115 for mounting the outlet passageway 106 on the container 102.

The inlet passageway 104 and the outlet passageway 106 may be formed of any non-toxic, non-pyrogenic material suitable for molding. One example of a suitable material is natural rubber. Natural rubber also has the proper flexibility and resiliency to make it ideal for proper operation of the check valve 120.

Operation of the irrigator and evacuator 10, as depicted in FIGS. 1, 2 and 3, includes filling the bladder with irrigating solution by any of the means mentioned above. Once the bladder is full with irrigating solution, the outlet passageway 30 is closed by the cap 32 and the evacuation fluid conduit 28 is connected at its first end 25 to the inlet passageway 26 and the openings 29 in its second end is placed in fluid flow communication with the wound. The evacuation fluid conduit 28 is obturated by means of a common clamp 21. The first end 23 of the irrigation fluid conduit 27 is connected in fluid flow communication with the second opening 46 of the bulbous member 44 and the openings 29 in its second end of the irrigation fluid conduit 27 is placed in fluid flow communication with the fluid in the wound. Unclamping the evacuating fluid conduit 28 will permit the irrigating solution to flow out of the bladder 40 and into the wound site where it will migrate to the openings 29 in the second end of the evacuating fluid conduit 28 along with any wound exudate which will flow into the container.

Through the cycle of use of the irrigator and evacuator, the quantity of exudate and irrigation solution received into the irrigator and evacuator 10 will equal the amount of irrigation solution dispensed from the bladder. Therefore, with the wound exudating, there will of necessity accumulate a quantity of fluid in excess of the quantity of irrigation solution placed in the wound. This excess will have to be removed by sealing the irrigation fluid conduit 29 closed with a common clamp, disconnecting the irrigation fluid conduit 27 from the irrigator and evacuator 10, emptying the container 12 and reactivating the irrigator and evacuator 10 by pumping the bulbous member 44 to inflate the bladder 40 with air and suctioning the accumulated excess wound fluid into the container 12 in a normal wound suctioning manner.

The small diameter of the bleed valve holes 58 and 59 provide a fixed, limiting value for the flow rate of the irrigation solution to the wound site. Additional variable flow rate may be obtained by having a stop-cock in series with the irrigation fluid conduit 27 and the bulbous member 44. Alternatively, the irrigation fluid conduit 27 may be controllably pinched and partially closed using hemostats or other types of pinch clamps. Throttling of the irrigation fluid conduit 27 is preferable to throttling the evacuation fluid conduit 28 to avoid the possibility of clogging the evacuation fluid conduit 28.

For reliable and expeditious irrigation and evacuation as disclosed herein, the irrigator and evacuator 10 should be operated initially by having both the irrigation and evacuation fluid conduits 27, 28 approximately the same length and by holding the irrigator and evacuator 10 and the fluid conduits 27, 28 at approximately the same vertical elevation as the wound site until both irrigation and evacuation fluid conduits 27, 28 are full with liquid, e.g. irrigation fluid filling the irrigation fluid conduit 27 and irrigation and/or exudate fluid filling the evacuation fluid conduit 28. After this initial step, the container may be positioned at any vertical height, either above or below the wound site and the suction level (negative pressure) conducted through the evacuation fluid conduit 28 to the wound site will remain relatively constant throughout the filling range of the container.

The irrigation fluid conduit 27 has no effect on the suction value, as the effect of the height of the liquid in the irrigation fluid conduit 27 is cancelled or negated by the equal height of the liquid in the evacuation fluid conduit 28. Because of this cancellation effect of the liquid in these conduits, the same suction value is obtained on the wound site regardless of the height of the container either above or below the wound site. The rate of fluid flow of the exudate and/or irrigation fluid from the wound into the container must always equal the rate of fluid flow of irrigation fluid into the wound site.

The irrigating solution used may be one of any number of medicinally acceptable fluids. Examples of such irrigating fluids are sterile, normal saline solution with or without an antibiotic, a penicillin detergent solution, or a currently-marketed brand of irrigating fluid such as American Cyanamid's "Aerosol Wash."

Although the embodiment of FIGS. 1-15 utilizes the bulbous member 44 to inflate the bladder 40, another embodiment of the present invention allows the bladder 40 to be inflated by deformation of the container. FIGS. 21 and 22 depict another embodiment of the instant invention wherein the container 11 is resilient and deformable. FIG. 21 shows the container 11 deformed by manual squeezing of the side walls 15 and 17 and FIG. 22 depicts the bladder 40 having been inflated and filled by releasing the side walls 15 and 17.

In this embodiment, there is no need for the bulbous member 44. The bladder 40 is filled by placing the axial passageway 52 in the plug 50 in fluid flow communication with irrigating solution at atmospheric pressure as depicted in FIG. 9. Pressing the resilient side walls 15 and 17 allows the air within the container 11 to escape through the outlet passageway 30 and after closing the outlet passageway 30 releasing the resilient side walls 15 and 17 creates a vacuum within the container 11 expanding the bladder 40 and aspirating the irrigating solution through the fluid conduit means 9 to fill the bladder 40.

This embodiment depicted in FIGS. 21 and 22 is used as previously disclosed with respect to the first embodiment.

Also it should be mentioned that the embodiment of FIGS. 21 and 22 may be used to provide filling of the bladder 40 by irrigation solution pre-stored in the container 12 as discussed above in reference to FIG. 11. However such filling with respect to FIGS. 21 and 22 embodiment will require the use of a tubing 97 of resilient material which can expand with each squeezing of the container sides at the solution forced from the container enters this tubing for temporary storage prior to being able to flow into the bladder 40 which occurs each time the container 12 sides are released.

The teachings of the co-pending application Ser. No. 587,142, filed on June 16, 1975 provide additional information with respect to the details of the resilient self-contained fluid evacuator and, when combined with the teachings of this application, fully disclose the second embodiment of this invention.

While the two embodiments of the invention have been illustrated and described, it will be appreciated by those skilled in the art and others that various changes can be made therein without departing from the spirit or scope of the invention. Hence, the invention can be practiced otherwise than specifically described herein.

What is claimed is:

1. A self-contained, combined irrigator and evacuator for use in bathing a wound with an irrigating liquid and removing liquid from the wound, comprising:
   (a) a container having an irrigation port communicating with the interior of the container;
   (b) a resilient, inflatable member within said container having a single opening in fluid-flow communication with said irrigation port;
   (c) an inlet passageway and an outlet passageway communicating with the interior of said container;
   (d) means in fluid-flow communication with said irrigation port for simultaneously inflating and filling said inflatable member against its resilient bias with said irrigating liquid;
   (e) flow control means in the opening of the inflatable member for enabling said inflating and filling means to inflate and fill said inflatable member against its bias with said irrigating liquid and for restricting the rate the bias of said inflatable member expels irrigating liquid from said inflatable member;
   (f) means for sealingly attaching said inflatable member opening to said irrigation port; and
   (g) means for selectively opening and closing said outlet passageway and said inlet passageway so that, as the bias of said inflatable member expels irrigating liquid from said inflatable member through said irrigation port, negative pressure created in said container due to deflation of said inflatable member may be used to aspirate fluid through said inlet passageway.

2. The irrigator and evacuator as in claim 1 wherein said container includes first and second spaced apart opposed side walls, third and fourth spaced apart side walls joined to the opposite ends of said first and second side walls, said third and fourth side walls being spaced apart a greater distance than said first and second walls, and a bottom wall joined to all four side walls, said four side walls joined together at their tops to form said irrigation port.

3. The irrigator and evacuator as in claim 2 also including means on said inlet passageway for permitting attachment of a fluid conduit means thereto in fluid-flow communication with said inlet passageway and wherein said third and fourth side walls have a configuration which substantially conforms to the natural, unimpeded shape of the adjacent portion of said inflatable member when inflated, deflation of said inflatable member effecting substantially constant negative pressure at said inlet passageway and providing positive irrigation pressure at the opening of said inflatable member.

4. The irrigator and evacuator as in claim 3 wherein said inflatable member is a substantially cylindrical resilient bladder and wherein said first and second side walls are substantially flat giving said container a low profile.

5. The irrigator and evacuator as in claim 4 wherein said inlet passageway is in one of said third and fourth side walls and said outlet passageway is in the other of said third and fourth side walls, said passageways being proximate to and on opposite sides of said irrigation port.

6. A self-contained combined irrigator and evacuator for use in bathing a wound with an irrigated liquid and removing liquid from the wound, comprising:
  (a) a substantially rigid container having substantially flat first and second spaced apart side walls, third and fourth side walls joined to the opposite ends of and spaced apart farther than said first and second side walls, and a bottom wall joining all four side walls, said four side walls being joined at their tops to form an irrigation port communicating with the interior of said container;
  (b) a substantially cylindrical, resilient bladder having a single opening, said bladder being within said container and said bladder opening being in fluid flow communication with said irrigation port, said third and fourth side walls having a configuration substantially conforming to the natural, unimpeded shape of the adjacent portion of said bladder when inflated;
  (c) an inlet passageway in one of said third and fourth side walls and an outlet passageway in the other of said third and fourth side walls, said passageways communicating with the interior of said container and being proximate to and on opposite sides of said irrigation port;
  (d) means for selectively permitting and preventing fluid flow through said passageways;
  (e) means in fluid-flow communication with said irrigation port for simultaneously inflating and filling said bladder against its resilient bias with said irrigating liquid; and
  (f) means for preventing fluid flow between the interior of said bladder and the interior of said container exterior said bladder, the former being a pressure-irrigating section wherein the bias of the bladder when inflated and filled tends to expel said irrigating liquid under positive pressure through said irrigation port and the latter being a suction-evacuating section wherein deflation of said bladder creates a negative pressure in said container which may be used to aspirate fluid through said inlet passageway.

7. The irrigator and evacuator as in claim 6 also including flow control means in the opening of said bladder for enabling said inflating and filling means to inflate and fill said bladder with said irrigating liquid and for restricting the rate the bias of said bladder expels irrigating liquid from said bladder.

8. The irrigator and evacuator as in claim 7 wherein said inflating means is a hand-operated, resilient bulbous member exterior to said container having a neck portion defining an opening and a second opening opposite said neck opening, the resiliency of said bulbous member being greater than that of said bladder, the neck of said bulbous member being mounted in fluid flow communication with said bladder opening through said irrigation port such that obturation of said second opening and compression of said bulbous member forces fluid from said bulbous member into said bladder against the bias of said bladder.

9. The combined irrigator and evacuator as in claim 8 wherein said flow control means comprises two one-way check valves each having a bleed valve therein, one check valve being mounted on and controlling flow through said second opening of said bulbous member and the other check valve being mounted on and controlling flow through said neck opening, said check valves permitting fluid flow into said bulbous member and into said bladder at a higher rate than said bleed valves permit fluid to flow from said bladder and from said bulbous member.

10. The combined irrigator and evacuator as in claim 9 also including means on the second opening of said bulbous member for permitting attachment of a fluid conduit thereto in fluid flow communication with said second opening.

11. The combined irrigator and evacuator as in claim 10 wherein said means for inflating and filling said bladder comprises a filling fluid conduit being at one end attached to said attachment means on and in fluid flow communication with said second opening of said bulbous member and at the other end in fluid flow communication with contained irrigating liquid at atmospheric pressure, repetitive squeezing and releasing of said bulbous member inflating and filling said bladder against its resilient bias with said irrigating liquid, said bias tending to expel said irrigating liquid and, with said outlet port obturated, creating a negative pressure at said inlet passageway.

12. The combined irrigator and evacuator as in claim 11 also including an irrigating fluid conduit and an evacuating fluid conduit, each of said conduits being open at a first end and having a plurality of openings at the second end for being placed in fluid flow communication with liquid in said wound, the first end opening of said irrigating fluid conduit being attached to said attachment means on and in fluid flow communication with said second opening of said bulbous member for conducting said irrigating liquid expelled from said bladder to said wound and the first end opening of said evacuating fluid conduit being attached to and in fluid flow communication with said inlet passageway for conducting liquid from said wound to said container.

13. The combined irrigator and evacuator as in claim 10 wherein said means for inflating and filling said bladder comprises a filling fluid conduit being at one end attached to said attachment means on and in fluid flow communication with said second opening of said bulbous member and at the other end in fluid flow communication with contained, pressurized irrigating liquid, said pressurized irrigating liquid being forced against said resilient bias into and inflating said bladder.

14. The combined irrigator and evacuator as in claim 10 wherein said means for inflating and filling said bladder comprises two filling fluid conduits, one being at one end attached to and in fluid flow communication with said inlet port and the other end being in fluid flow communication with an external vacuum source and the other filling fluid conduit being at one end in fluid flow communication with the second opening of said bulbous member and at the other end in fluid flow communication with contained irrigating liquid at atmospheric pressure such that the external vacuum source tends to expand such bladder against said bias creating a negative pressure in said bladder for aspirating irrigating liquid into and filling said bladder.

15. A self-contained, combined irrigator and evacuator for use in bathing a wound with an irrigating liquid and removing liquid from the wound, comprising:
 (a) a substantially rigid container having substantially flat first and second spaced apart side walls, third and fourth side walls joined to the opposite ends of and spaced apart farther than said first and second side walls, and a bottom wall joining all four side walls, said four side walls being joined at their tops to form an irrigation port communicating with the interior of said container;
 (b) a substantially cylindrical, resilient bladder having a single opening, said bladder being within said container and said bladder opening being in fluid flow communication with said irrigation port, said third and fourth side walls having a configuration substantially conforming to the natural, unimpeded shape of the adjacent portion of said bladder when inflated;
 (c) an inlet passageway in one of said third and fourth side walls and an outlet passageway in the other of said third and fourth side walls, said passageways communicating with the interior of said container and being proximate to and on opposite sides of said irrigation port;
 (d) means for selectively permitting and preventing fluid flow through said passageways;
 (e) a hand-operated, resilient bulbous member exterior to said container having a neck portion defining an opening and a second opening opposite said neck opening, the resiliency of said bulbous member being greater than that of said bladder, the neck of said bulbous member being mounted in fluid flow communication with said bladder opening through said irrigation port;
 (f) flow control means mounted on and controlling flow through said neck opening and mounted on and controlling flow through said second opening of said bulbous member for enabling compression of said bulbous member to inflate and fill said bladder against its bias with irrigating liquid at a higher rate than liquid can be expelled from said bladder by its resilient bias;
 (g) means on said second opening of said bulbous member for permitting attachment of a fluid conduit in fluid flow communication with said bulbous member;
 (h) means on said outlet passageway for selective obturation of said outlet passageway; and
 (i) means for sealingly attaching said bladder opening to said neck opening of said bulbous member.

16. The combined irrigator and evacuator as in claim 15 wherein said flow control means are two one-way check valves each having a bleed valve therein, the check valves permitting fluid flow into said bulbous member and into said bladder at a higher rate than said bleed valves permit fluid to flow from said bladder and from said bulbous member.

17. The combined irrigator and evacuator as in claim 15 also including an inwardly extending tubular protuberance around said outlet passageway, said protuberance extending into the container a distance calculated to bring it in contact with the bladder at the appropriate bladder inflation level.

18. The combined irrigator and evacuator as in claim 17 wherein said bladder on inflation occludes said inward protuberance and said outlet passageway when said bladder and said third and fourth side walls obtain a predetermined relationship thereby terminating the expulsion of fluid from the container, said predetermined relationship being that further inflation of said bladder without occlusion of said outlet passageway would produce deformation of said inflatable member into a shape which it would not if said third and fourth walls were non-existent.

19. The combined irrigator and evacuator as in claim 15 including means for storing said irrigating liquid comprising transfer fluid conduit means for providing fluid flow communication between said outlet passageway and said second opening of said bulbous member and one-way flow control means permitting fluid flow through said transfer fluid conduit means from said outlet passageway to said bulbous member second opening, said irrigating liquid being stored in the interior of said container external said bladder and said irrigating liquid being pumped from said container to said bladder by repetitive squeezing and releasing of said bulbous member to charge said bladder prior to using.

20. The combined irrigator and evacuator as in claim 15 also including a flexible coating covering the interior surface of said bladder and said bulbous member, said coating being of a material having low vapor permeability, said coating permitting pre-filling and storing of said irrigating liquid in said bladder.

21. The combined irrigator and evacuator as in claim 15 also including a flexible liner forming a bag within and conforming to the shape of said bladder, the liner bag having an opening concentric with the opening in said bladder that is in fluid flow communication with said neck opening of said bulbous member and the liner being of a material having low vapor permeability thereby permitting prefilling and storage of said irrigating liquid in said bladder.

22. A method of concurrently irrigating and evacuating a wound site through the use of a single, portable device, comprising:
 (a) increasing the volume of a first chamber against a bias while simultaneously reducing the volume of a second chamber, said bias opposing said volume reduction;
 (b) filling said first chamber with an irrigating liquid;
 (c) connecting said first chamber to said wound site by a first fluid conduit means;
 (d) connecting said second chamber to said wound site by a second fluid conduit means;
 (e) permitting said bias to contract said first chamber thereby expelling said irrigating liquid from said first chamber to said wound site while simultaneously expanding the volume of said second chamber and creating a negative pressure in said second chamber; and (f) aspirating liquid from said wound site by means of said negative pressure created in said second chamber.

23. A self-contained, combined irrigator and evacuator for use in bathing a wound with an irrigating liquid and removing liquid from the wound, comprising:
(a) a resilient container having substantially flat first and second spaced apart side walls, third and fourth side walls joined to the opposite ends of and spaced apart farther than the first and second side walls, and a bottom wall joining all four side walls, the four side walls being joined at their tops to form an irrigation port communicating with the interior of said container;
(b) a substantially cylindrical, resilient bladder having a single opening, said bladder being within said container and said bladder opening being in fluid flow communication with said irrigation port, said third and fourth side walls having a configuration substantially conforming to the natural, unimpeded shape of the adjacent portions of said bladder when inflated;
(c) an inlet passageway in one of said third and fourth side walls and an outlet passageway in the other of said third and fourth side walls, said passageways communicating with the interior of said container and being proximate to and on opposite sides of said irrigation port;
(d) means for selectively permitting and preventing fluid flow through said passageways;
(e) flow control means mounted on and controlling flow through said irrigation port for enabling inflating and filling said bladder against its resilient bias with said irrigating liquid and for restricting the rate the bias of said bladder expels irrigating liquid from said bladder, said flow control means permitting squeezing and releasing the first and second side walls of said container creating negative pressure in said bladder for aspirating said irrigating liquid into and filling said bladder against said bias;
(f) means on said irrigation port for permitting attachment in fluid flow communication of a fluid conduit; and
(g) means for sealingly attaching said bladder opening to said irrigation port, whereby the bias of said bladder tends to expel said irrigating liquid through said irrigation port and deflate said bladder, with said outlet passageway obturated, creates negative pressure in said container at said inlet passageway.

* * * * *